United States Patent
Sullivan et al.

(10) Patent No.: US 7,227,628 B1
(45) Date of Patent: Jun. 5, 2007

(54) WAFER INSPECTION SYSTEMS AND METHODS FOR ANALYZING INSPECTION DATA

(75) Inventors: Paul Sullivan, Campbell, CA (US); George Kren, Los Altos Hills, CA (US); Eliezer Rosengaus, Palo Alto, CA (US); Patrick Huet, San Jose, CA (US); Robinson Piramuthu, San Jose, CA (US); Martin Plihal, Pleasanton, CA (US); Yan Xiong, Sunnyvale, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

(21) Appl. No.: 10/964,585

(22) Filed: Oct. 12, 2004

Related U.S. Application Data

(60) Provisional application No. 60/510,709, filed on Oct. 10, 2003.

(51) Int. Cl.
*G01N 21/88* (2006.01)
*G06K 9/00* (2006.01)

(52) U.S. Cl. .............................. 356/237.4; 356/237.2; 382/145; 250/559.46

(58) Field of Classification Search .. 356/237.1–237.6; 250/559.4, 559.45, 559.29, 221, 223 R; 414/935–936; 382/145, 153, 154; 118/52, 118/666; 700/121, 100
See application file for complete search history.

(56) References Cited

U.S. PATENT DOCUMENTS

| | | | | |
|---|---|---|---|---|
| 4,644,172 A | * | 2/1987 | Sandland et al. | 250/548 |
| 4,907,931 A | * | 3/1990 | Mallory et al. | 414/744.6 |
| 5,264,912 A | * | 11/1993 | Vaught et al. | 356/237.5 |
| 5,814,829 A | * | 9/1998 | Broude et al. | 250/559.46 |
| 5,909,276 A | * | 6/1999 | Kinney et al. | 356/237.2 |
| 5,917,588 A | * | 6/1999 | Addiego | 356/237.2 |
| 5,940,175 A | * | 8/1999 | Sun | 356/237.3 |
| 6,062,084 A | * | 5/2000 | Chang et al. | 73/601 |
| 6,201,601 B1 | | 3/2001 | Vaez-Iravani et al. | |
| 6,204,917 B1 | | 3/2001 | Smedt | |
| 6,271,916 B1 | | 8/2001 | Marxer et al. | |
| 6,320,402 B1 | * | 11/2001 | Phan et al. | 324/765 |
| 6,399,957 B1 | * | 6/2002 | Murata | 250/559.4 |
| 6,424,733 B2 | * | 7/2002 | Langley | 382/145 |

(Continued)

FOREIGN PATENT DOCUMENTS

WO 99/59200 11/1999

*Primary Examiner*—Sang H. Nguyen
(74) *Attorney, Agent, or Firm*—Baker & McKenzie LLP

(57) ABSTRACT

Wafer inspection systems and methods are provided. One inspection system includes a module measurement cell coupled to a host inspection system by a wafer handler. The module measurement cell is configured to inspect a wafer using one or more modes prior to inspection of the wafer by the host inspection system. The one or more modes include backside inspection, edge inspection, frontside macro defect inspection, or a combination thereof. Another inspection system includes two or more low resolution electronic sensors arranged at multiple viewing angles. The sensors are configured to detect light returned from a wafer substantially simultaneously. A method for analyzing inspection data includes selecting a template corresponding to a support device that contacts a backside of a wafer prior to inspection of the backside of the wafer. The method also includes subtracting data representing the template from inspection data generated by inspection of the backside of the wafer.

30 Claims, 3 Drawing Sheets

U.S. PATENT DOCUMENTS

| | | |
|---|---|---|
| 6,452,671 B1 * | 9/2002 | Uda et al. ................ 356/237.2 |
| 6,538,730 B2 | 3/2003 | Vaez-Iravani et al. |
| 6,553,323 B1 * | 4/2003 | Obara et al. .................. 702/35 |
| 6,559,938 B1 | 5/2003 | Smedt |
| 6,580,087 B1 * | 6/2003 | Suzuki et al. ............ 250/559.4 |
| 6,614,050 B1 * | 9/2003 | Yamada et al. ................ 257/48 |
| 6,630,995 B1 * | 10/2003 | Hunter .................... 356/237.5 |
| 6,963,394 B2 * | 11/2005 | Yamamoto et al. ...... 356/237.4 |
| 6,963,789 B2 * | 11/2005 | Bun et al. ................... 700/121 |

* cited by examiner

WAFER INSPECTION SYSTEMS AND METHODS FOR ANALYZING INSPECTION DATA

PRIORITY CLAIM

This application claims priority to U.S. Provisional Application No. 60/510,709 entitled "Wafer Inspection Systems and Methods for Analyzing Inspection Data," filed Oct. 10, 2003, which is incorporated by reference as if fully set forth herein.

BACKGROUND OF THE INVENTION

1. Field of the Invention

The present invention generally relates to inspection systems and methods. Certain embodiments relate to wafer inspection systems and methods for analyzing inspection data.

2. Description of the Related Art

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor fabrication process, defects such as particulate contamination and pattern defects may be introduced into semiconductor devices. Such defects may be found either randomly on a specimen surface or may be repeated within each device formed on a specimen. For example, random defects may be caused by events such as an unexpected increase in particulate contamination in a manufacturing environment and an unexpected increase in contamination in process chemicals used in fabrication of a semiconductor device. Defects may also be formed in a systematic fashion over time and due to individual process marginalities and interactions of multiple processes. Defects caused by individual process marginalities or by interactions between multiple processes may result in defects such as a film thickness variation or a lateral dimension variation due to dose variation. Such defects may, in turn, result in additional defects in a semiconductor device formed on the specimen such as bridging between two conductive structures thereby forming a short between the structures. Defects repeated within each semiconductor device formed on an entire specimen may, for example, be systematically caused by contamination or defects found on a reticle, or a mask. Contamination or defects on a reticle may be transferred along with a device pattern to a resist during a lithography process.

As the dimensions of advanced semiconductor devices continue to shrink, the presence of defects in the semiconductor devices limits the successful fabrication, or yield, of a semiconductor device. For example, a reticle defect reproduced in a resist patterned during lithography may cause an open circuit or a short circuit in a semiconductor device formed in subsequent processing. Because fabrication of a semiconductor device includes many complex process steps, the adverse effects of defects on total yield may increase exponentially if an error that is caused by a defect is propagated throughout an entire manufacturing process or operation over time.

SUMMARY OF THE INVENTION

An embodiment of the invention relates to an inspection system that includes a module measurement cell coupled to a host inspection system by a wafer handler. The module measurement cell is configured to inspect a wafer using one or more modes prior to inspection of the wafer by the host inspection system. In one embodiment, the one or more modes may include backside inspection, edge inspection, frontside macro defect inspection, or a combination thereof. In some embodiments, the module measurement cell may be configured to perform frontside macro defect inspection as the wafer is being moved into the module measurement cell by the wafer handler. In addition, the module measurement cell may include an optical character recognition (OCR) subsystem, a barcode reader (BCR) subsystem, an alignment subsystem, or a combination thereof. In some embodiments, the host inspection system may be configured to inspect an additional wafer while the module measurement cell is inspecting the wafer.

In an additional embodiment, the module measurement cell may be configured as an additional host inspection system. Therefore, in this embodiment, the system includes two host inspection systems coupled by a wafer handler. One of the host inspection systems is configured to perform "preliminary" inspection of a wafer, and the other host inspection system is configured to perform "primary" inspection of the wafer. Preliminary inspection may include backside inspection, edge inspection, frontside macro defect inspection, or a combination thereof.

The inspection system also includes a processor coupled to at least the module measurement cell. The processor is configured to detect defects on the wafer using output produced by the module measurement cell. In one embodiment, the processor may be configured to use the output to determine if the inspection of the wafer by the host inspection system is to be performed. In another embodiment, the processor may be configured to use the output to determine if the wafer must be reworked and to determine that the wafer is not to be inspected by the host inspection system if the wafer must be reworked. In an additional embodiment, the processor may be configured to use the output to determine if the wafer has backside contamination above a predetermined level. In such an embodiment, the processor may also be configured to determine that the wafer is not to be inspected by the host inspection system if the backside contamination is above the predetermined level. The system may be further configured as described herein.

Another embodiment relates to a different inspection system. This system includes an illumination subsystem configured to direct light to a wafer. In one embodiment, the illumination subsystem includes a point light source. In one such embodiment, the illumination subsystem may include one or more optical filters coupled to the point light source. The one or more optical filters may be configured to alter a wavelength spectrum of the light directed to the wafer. In some embodiments, the light directed to the wafer may be collimated light. In another embodiment, the system may include an additional illumination subsystem. The illumination subsystem and the additional illumination subsystem may be configured to direct light to the wafer at different azimuthal angles.

The system also includes two or more low resolution electronic sensors arranged at multiple viewing angles. The two or more sensors are configured to detect light returned from the wafer substantially simultaneously. In one embodiment, the two or more sensors may include CCD cameras, and output produced by the sensors may include direct digital readouts. In some embodiments, the multiple viewing angles may be substantially constant during inspection. In another embodiment, a position of the wafer may be substantially constant during inspection. In an additional embodiment, the system may include a support device that is configured to spin the wafer during inspection. In some embodiments, the system may include imaging optics coupled to the two or more sensors. Optical axes of the imaging optics may not be normal to sensor arrays of the two or more sensors.

In addition, the system includes a processor configured to detect defects on the wafer using output generated by the two or more sensors. The defects may be defocus defects, relatively small pattern defects, or a combination thereof. In one embodiment, the output includes images, and the processor may be configured to assign common coordinates to the images and to compare the images produced by different sensors. In another embodiment, the processor may also be configured to determine which of the two or more sensors produces images with the largest sensitivity to defocus defects. In one such embodiment, the processor may further be configured to select the images with the largest sensitivity for use in defect detection.

In some embodiments, the inspection system may be coupled to a wafer handler of a host inspection system. For example, this inspection system may be included in the module measurement cell described above. In a different embodiment, the inspection system may be coupled to a wafer handler of a process tool. This inspection system may be further configured as described herein.

An additional embodiment relates to a computer-implemented method for analyzing inspection data. The method includes selecting a template that corresponds to a support device that contacts a backside of a wafer prior to inspection of the backside of the wafer. In one embodiment, the support device may be a chuck, a stage, an aligner, or a wafer handler.

In some embodiments, the method may include creating the data representing the template using computer-aided design. In a different embodiment, the method may include creating the data representing the template by inspecting a backside of two or more wafers contacted by the support device and extracting common information from inspection data generated by the backside inspection of the two or more wafers.

The method also includes subtracting data representing the template from the inspection data generated by inspection of the backside of the wafer to generate data representing defects on the backside of the wafer. The defects on the backside of the wafer may include defects caused by the support device such as contamination. In one embodiment, the method may include subtracting the data representing the defects from data generated by inspection of a frontside of a wafer. Alternatively, prior to subtracting the data representing the template, the inspection data may be generated by subtracting backside inspection data from data generated by inspection of a frontside of the wafer. In an additional embodiment, the method may include correlating the defects on the backside of the wafer to defects detected on a frontside of the wafer. In some embodiments, the method may also include classifying the defects. The method may also include any other steps described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
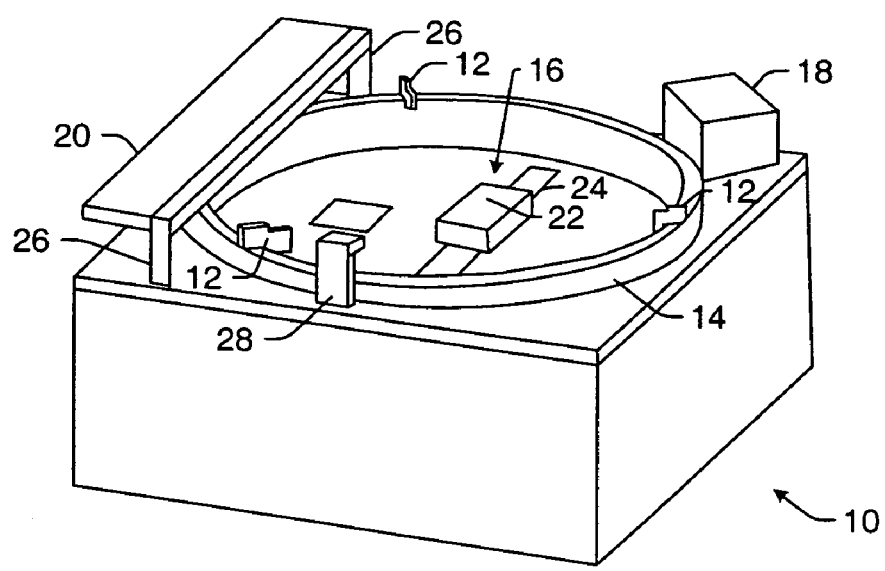
FIG. 1 is a schematic diagram illustrating a perspective view of an embodiment of a module measurement cell that may be coupled to a host inspection system.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers formed upon a substrate. For example, such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical (MEMS) devices and the like may also be formed on a wafer.

In the case of a wafer, the term "frontside" is generally defined as the surface of the wafer upon which semiconductor devices will be or have been formed, and the term "backside" is generally defined as the surface of the wafer upon which semiconductor devices will not be formed. Although the frontside of a wafer is usually polished, the backside of a wafer may be unpolished (i.e., a single-sided polish wafer) or polished (i.e., a double-sided polish wafer).

Turning now to the drawings, it is noted that FIGS. 1–4 are not drawn to scale. In particular, the scale of some of the elements of the figures are greatly exaggerated to emphasize characteristics of the elements. It is also noted that FIGS. 1–4 are not drawn to the same scale. Elements shown in more than one figure that may be similarly configured have been indicated using the same reference numerals.

FIG. 1 illustrates module measurement cell 10. A wafer (not shown) may be disposed in the measurement cell by a wafer handler (not shown). The wafer may be placed on supports 12 coupled to wafer carrier ring 14. Although three supports are shown coupled to wafer carrier ring 14, it is to be understood that more than three supports may be coupled to the wafer carrier ring. The wafer carrier ring may include any appropriate carrier ring known in the art. In some embodiments, the wafer carrier ring may be configured to rotate such that various functions can be performed on different portions of the wafer.

The module measurement cell is configured to inspect a wafer using one or more modes. The one or more modes may include backside inspection, edge inspection, frontside macro defect inspection, or a combination thereof. For example, the measurement cell includes backside inspection subsystem 16, edge inspection subsystem 18, and frontside macro defect inspection subsystem 20.

The backside inspection subsystem is arranged such that this subsystem can inspect the backside of a wafer while the wafer is disposed within the carrier ring. In some embodiments, the backside inspection subsystem may include measurement head 22. The measurement head may be configured to detect defects on the backside of a wafer using a variety of modes such as brightfield inspection and/or darkfield inspection. The measurement head may include any suitable optical components known in the art.

Measurement head 22 may be configured to move laterally along track 24 such that the backside inspection subsystem may inspect various locations on the backside of a wafer. In addition, while the measurement head is inspecting the backside of the wafer for defects, carrier ring 14 may be configured to rotate the wafer. In this manner, the backside inspection system may be configured to inspect the backside of the wafer in two dimensions (i.e., r and θ). In some embodiments, the backside inspection system may be configured to inspect approximately the entire backside of the wafer. In addition, measurement head 22 and/or backside inspection subsystem 16 may have other configurations such as those described in U.S. Pat. No. 6,204,917 to Smedt and U.S. Pat. No. 6,559,938 to Smedt, which are incorporated by reference as if fully set forth herein.

Edge inspection subsystem 18 is arranged such that the subsystem can inspect an outer edge of a wafer while the wafer is disposed within the carrier ring. Examples of defects that may be found on the outer edge of wafers include, but are not limited to, chips, cracks, scratches, marks, particles, and residual chemicals (e.g., resist and slurry). The edge inspection subsystem may have a fixed position within the measurement cell. However, the edge inspection subsystem may inspect substantially the entire outer edge of a wafer as the wafer is being rotated in the carrier ring. In other embodiments, the edge inspection subsystem may be configured to move with respect to the carrier ring. Such an embodiment may be suitable if the measurement cell does not include other subsystems in fixed positions around the carrier ring or if these other subsystems are also configured to move in conjunction with the edge inspection subsystem. In such embodiments, the carrier ring may be configured to rotate as well in a direction opposite to the movement of the edge inspection subsystem, or the carrier ring may remain in one position.

One position of the edge inspection subsystem within measurement cell 10 is illustrated in FIG. 1. It is to be understood, however, that the edge inspection subsystem may also be placed at any other suitable position around the carrier ring. In addition, the edge inspection subsystem may inspect the edge of the wafer while the backside inspection subsystem is inspecting the backside of the wafer. In this manner, the measurement cell has a greater throughput than if the backside inspection and edge inspection were performed serially. One example of a commercially available edge inspection system is the EdgeScan system, which is commercially available from Raytex Corporation, Tokyo, Japan. Edge inspection subsystem 18 may have an optical configuration that is similar to that of the EdgeScan system.

Frontside macro defect inspection subsystem 20 is arranged such that the subsystem can detect macro defects on a frontside of a wafer. The term "macro defects" generally refers to defects having a lateral dimension greater than about 25 µm. Such large scale defects may include resist or developer problems such as lifting resist, thin resist, extra photoresist coverage, incomplete or missing resist which may be caused by clogged dispense nozzles or an incorrect process sequence, and developer or water spots. Additional examples of macro defects may include regions of defocus caused by particles on the backside of a wafer ("hot spots"), reticle errors such as tilted reticles, out-of-focus exposure or incorrectly selected reticles, scratches, pattern integrity problems such as over or under developing of the resist, contamination such as particles or fibers, and non-uniform or incomplete edge bead removal (EBR).

Subsystem 20 may inspect the frontside of a wafer while the wafer is being moved into the module measurement cell by a wafer handler. For example, a wafer handler may move a wafer underneath the frontside inspection subsystem while the wafer handler is placing the wafer into the measurement cell or removing the wafer from the measurement cell. In such an embodiment, the frontside inspection subsystem may inspect the frontside of the wafer as the wafer handler is moving the wafer underneath the frontside inspection subsystem.

Frontside inspection subsystem 20 has a lateral dimension that is approximately equal to or greater than a diameter of a wafer. In one embodiment, the frontside inspection subsystem may include linear-based optics (e.g., a linear-based light source, a linear array of lenses, and a linear array of detectors) such that the frontside inspection subsystem can scan substantially an entire line across the wafer substantially simultaneously. Examples of linear-based optics that may be suitable for frontside inspection subsystem 20 are illustrated in U.S. patent application Ser. No. 09/965,408 entitled "Systems and Methods for Inspection of Specimen Surfaces," filed Sep. 25, 2001, which is incorporated by reference as if fully set forth herein. Alternatively, the frontside inspection subsystem may include optics configured to scan the wafer in a direction substantially perpendicular to the direction in which the wafer handler moves the wafer. In this manner, the frontside inspection subsystem may scan the wafer in a serpentine-like path. The frontside inspection subsystem may be configured to detect defects on the frontside of the wafer using a variety of modes such as brightfield inspection and/or darkfield inspection.

In the above described embodiments, the position of the frontside inspection subsystem may be substantially constant during inspection. However, in other embodiments, the frontside inspection subsystem may be configured to move over the wafer while the wafer is disposed within the carrier ring. For example, the frontside inspection subsystem may be configured to pivot on one or the other of supports 26 such that the frontside inspection subsystem can scan the frontside of a wafer while the wafer is within the carrier ring. Obviously, in such an embodiment, the subsystem would include only one such support such that the subsystem clears the top of the carrier ring during a scan.

In some embodiments, the module measurement cell may perform a number of additional functions. For example, the module measurement cell may include an optical character recognition (OCR) subsystem, a barcode reader (BCR) subsystem, an alignment subsystem, or a combination thereof. The OCR subsystem (not shown) may be configured to detect and recognize alphanumeric characters permanently formed in a wafer, which serve as identification for the wafer. The OCR subsystem may include any appropriate OCR system known in the art. Similarly, the BCR subsystem (not shown) may be configured to detect and read a barcode permanently formed in a wafer, which serves as identification for the wafer.

In addition, alignment subsystem 28 may include a "notch finder" or a "flat finder." Generally, an alignment subsystem may be configured to direct light at the frontside or backside of a wafer near the outer edge of the wafer. The alignment subsystem may also be configured to detect light reflected by the wafer or to detect light transmitted by the wafer. When the alignment subsystem detects an abrupt change in the detected light, the alignment subsystem will indicate that the position on the wafer corresponding to the change is the location of the notch or flat. The alignment subsystem may also include any appropriate configuration known in the art. The location of the detected notch or flat may be used as a reference to move the wafer into a desired position prior to the start of inspection.

The OCR subsystem, the BCR subsystem, and/or the alignment subsystem may be configured to scan the wafer while the wafer is being rotated by the carrier ring. Alternatively, the OCR subsystem, the BCR subsystem, and/or the alignment subsystem may be configured to scan the wafer while the subsystem(s) are rotated around the carrier ring. In addition, the OCR subsystem, the BCR subsystem, and/or the alignment subsystem may be configured to scan the wafer substantially simultaneously or serially. In some embodiments, the OCR subsystem, the BCR subsystem, and/or the alignment subsystem may be configured to scan the wafer while the measurement cell is inspecting the wafer in one or more modes. For example, in one embodiment, the alignment subsystem may scan the wafer for a notch or a flat while the edge inspection subsystem and/or the backside inspection subsystem are inspecting the wafer.

As can be seen from the above description, the module measurement cell, which may also be referred to as a "multifunction inspection module," is a modular system having several inspection functions combined with an OCR subsystem, BCR subsystem, and/or a notch/flat aligner, all coupled to a wafer handler. Therefore, module measurement cell 10 performs a number of functions that are traditionally performed prior to inspection (OCR, BCR, and alignment). However, module measurement cell 10 is also configured to perform a number of other functions including backside inspection, edge inspection, frontside macro defect inspection, or some combination thereof. Therefore, in one embodiment, the module measurement cell may be advantageously coupled to a "host inspection system" such that the measurement cell can perform one or more of the above described functions prior to inspection by the host inspection system. In this manner, the module measurement cell provides pre-qualification of a wafer prior to main inspection in a host inspection system. Until now, these inspection functions have been performed by the host inspection system. The host inspection system typically performs these functions in a sequence, which reduces the throughput of the host inspection system.

As used herein, the term "host inspection system" refers to any system or module configured to perform frontside inspection of patterned or unpatterned wafers known in the art. Examples of such a system are illustrated in U.S. Pat. No. 6,201,601 to Vaez-Iravani et al., U.S. Pat. No. 6,271,916 to Marxer et al., and U.S. Pat. No. 6,538,730 to Vaez-Iravani et al., which are incorporated by reference as if fully set forth herein. A host inspection system also generally is configured as a stand alone tool since the throughput of such a system is relatively low. However, performing one or more functions of the host inspection system (e.g., alignment, edge inspection, etc.) with the module measurement cell in a background mode prior to inspection of a wafer by the host inspection system will dramatically increase the throughput of the host inspection system. Additional advantages of using a module measurement cell to perform one or more functions of a host inspection system are further described below.

Figure 2:
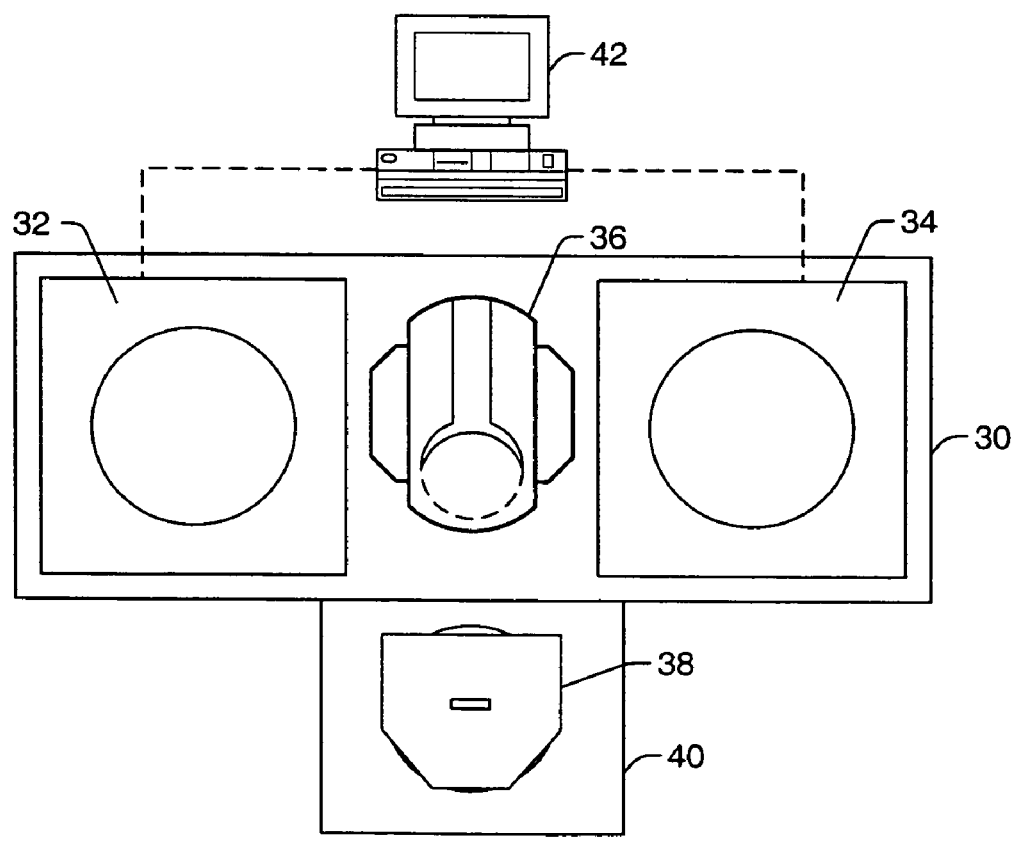
FIG. 2 is a schematic diagram illustrating a plan view of an embodiment of an inspection system that includes a module measurement cell coupled to a host inspection system by a wafer handler.

One embodiment of a system that includes a module measurement cell coupled to a host inspection system is illustrated in FIG. 2. As shown in FIG. 2, system 30 includes module measurement cell 32 coupled to host inspection system 34 by wafer handler 36. Although one type of robotic wafer handler is shown in FIG. 2, it is to be understood that the wafer handler may have any suitable configuration known in the art. For example, in some embodiments, an edge handling wafer handler may be preferable. Wafer handler 36 may be configured to remove a wafer from cassette 38 positioned in load module 40. Wafer handler 36 may then place the wafer into module measurement cell 32 such that the measurement cell can perform one or more of the functions described above on the wafer. In addition, the functions which are performed on particular wafers by the module measurement cell may be selected by a user. In this manner, all of the functions that a module measurement cell may be configured to perform may not be performed on every wafer. The user may select one or more of the functions depending on, for example, characteristics of the wafer, defects of interest, or the type of identification mark on the wafer. Module measurement cell 32 may be configured as described above.

In some embodiments, host inspection system 34 may inspect one wafer while the module measurement cell is performing one or more functions on another wafer. Preferably, as the host inspection system is finishing inspection of one wafer, the module measurement cell has already finished performing one or more functions on another wafer. In other words, the module measurement cell is preferably configured to perform one or more of the above described functions on a wafer in an amount of time equal to or shorter than that which the host inspection system takes to inspect a wafer. In this manner, the host inspection system may perform substantially continuous inspection of a number of wafers, which is interrupted only by the amount of time to move wafers into and out of the host inspection system. As such, the throughput of the inspection system may be dramatically increased due to the increased throughput of the host inspection system.

FIG. 2 illustrates only one arrangement of module measurement cell 32, host inspection system 34, wafer handler 36, and load module 40. One of ordinary skill in the art will recognize that many different configurations of inspection system 30 may be produced by re-arranging the different modules. In addition, system 30 may include additional components. For example, the system may include an additional wafer handler (not shown). In one such embodiment, load module 38 may be positioned on the side of module measurement cell 32 farthest from the host inspection system. In this embodiment, the additional wafer handler may be configured to remove the wafer from the cassette and to place it into the module measurement cell. Wafer handler 36 may then move the wafer from the module measurement cell to the host inspection system after the module measurement cell has performed one or more of the above described functions on the wafer.

The inspection system may also include more than one module measurement system. The module measurement systems may be similarly configured or may be differently configured. The module measurement systems may be configured to operate substantially simultaneously in parallel or to operate serially. In addition, or alternatively, the inspection system may include more than one host inspection system. The host inspection systems may also be configured similarly or differently. The host inspection systems may be configured to perform different mode(s) of inspection. In such an embodiment, the host inspection systems may inspect a wafer serially. Alternatively, the host inspection systems may be configured to perform the same mode of inspection. In one such embodiment, the host inspection systems may inspect different wafers simultaneously. In a further embodiment, the inspection system may include two or more host inspection systems, and at least one of the host inspection systems may be configured to perform one or more functions of the module measurement cell described above. In this manner, the "module measurement cell" may be configured as an additional host inspection module. As such, the module measurement cell may provide some of the functions described above outside of the host inspection system in a separate host inspection system.

System 30 also includes processor 42, as shown in FIG. 2. Processor 42 is coupled to at least the module measurement cell such that the processor can perform one or more of the functions described herein. Processor 42 may be coupled to the measurement cell by a transmission medium as shown by the dotted lines in FIG. 2. Processor 42 may also be coupled to host inspection system 34, as shown in FIG. 2. In this manner, module measurement cell 32 and host inspection system 34 may be coupled by a common wafer handler in addition to a common processor. However, a different processor (not shown) may be coupled to host inspection system. The two processors may be similarly configured or may be differently configured. In addition, the two processors may be coupled in some manner such that data may be shared between the module measurement cell and the host inspection system.

Processor 42 is configured to detect defects on a wafer using output produced by the module measurement cell. In this manner, the processor may be configured to detect backside defects, edge defects, and/or frontside macro defects on a wafer. The processor may use any defect detection algorithm or method known in the art to detect defects on the wafer. The processor may also be configured to detect optical characters, a barcode, a notch, or a flat on a wafer using output produced by the module measurement cell. Algorithms or methods that may be used by the processor to detect such features are also known in the art.

The processor may also be configured to determine one or more functions that are to be performed on the wafer. For example, the processor may be configured to use the output of the module measurement cell to determine if inspection of the wafer by the host inspection system is to be performed. In one particular embodiment, the processor may be configured to use the output of the module measurement cell to determine if the wafer must be reworked. In addition, the processor may be configured to determine that the wafer is not to be inspected by the host inspection system if the wafer must be reworked. In this manner, the overall throughput of the host inspection system may be improved by not inspecting the wafer in the host inspection system (which generally has a much longer cycle time than the module measurement cell) as a result of the module measurements (e.g., major defect types such as de-focus that warrant rework).

In another embodiment, the processor may be configured to use the output to determine if the wafer has backside contamination above a predetermined level. In such an embodiment, the processor may also be configured to determine that the wafer is not to be inspected by the host inspection system if the backside contamination is above the predetermined level. As such, the module measurement cell may increase the overall uptime availability of a host inspection system. For example, wafers with problems (e.g., significant backside contamination), which potentially could result in service intervention on a host inspection system thereby resulting in host inspection system downtime, may not be introduced into the host inspection system.

Furthermore, the module measurement cell may improve overall customer yield. For example, wafers with certain problems such as significant backside contamination may result in cross-contamination and subsequent yield loss on additional wafers measured in a host inspection system. Cross-contamination is particularly prevalent for vacuum (i.e., contact) based chucks on a host inspection system. Therefore, by not introducing such wafers into a host inspection system based on results produced by the module measurement cell, the module measurement cell may improve yield. The system may also incorporate edge handling of wafers to significantly minimize potential cross-contamination.

Figure 3:
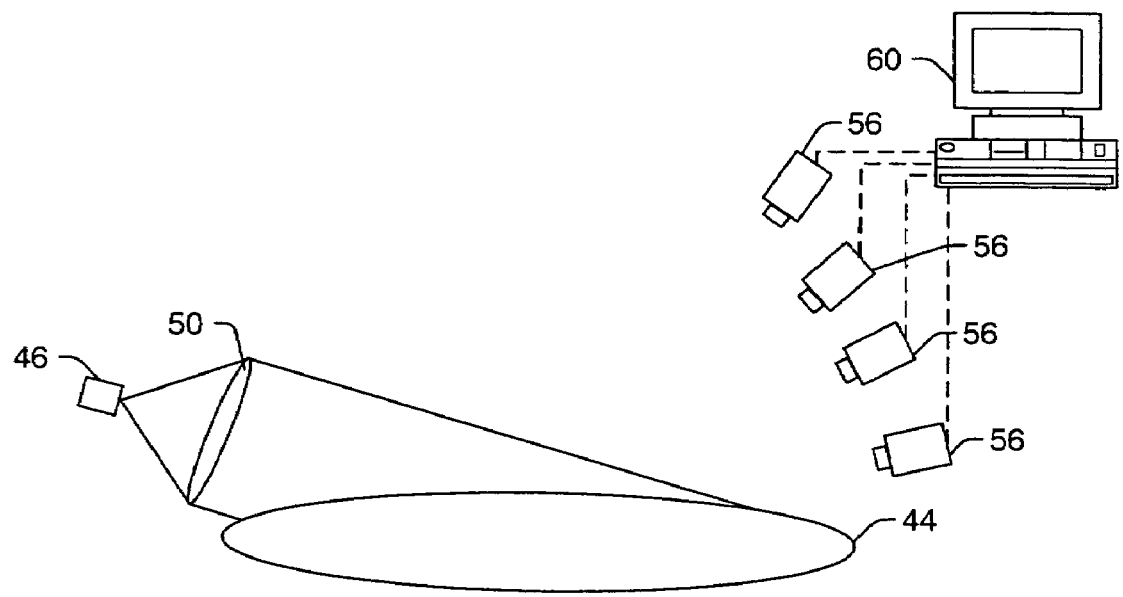
FIGS. 3 and 4 are schematic diagrams illustrating side views of various embodiments of an inspection system that includes multiple low resolution electronic sensors arranged at multiple viewing angles.

FIG. 3 illustrates one embodiment of a frontside macro defect inspection subsystem, which may be incorporated into the module measurement cell described above. However, this embodiment of the frontside macro defect inspection subsystem may also be utilized as a host inspection system in a stand-alone inspection system or an inspection system integrated into a process tool. The inspection subsystem illustrated in FIG. 3 includes a specialized imaging channel configured to detect several classes of macro defects or "macroscopic defects" on semiconductor wafers, particularly defocus defects.

Macroscopic wafer inspection in lithography has traditionally been done with human operators examining wafers mounted on tilt/spin tables (so called "Wafer wobblers") and detecting large-size defects present on the wafers. Alternatively, automated wafer inspectors have been built by KLA-Tencor, San Jose, Calif., (e.g., Models 2401 and 2430) and other companies (Nikon, ISOA, August Technologies, etc.). An important defect type of interest is optical defocus caused by either backside contamination, which causes the wafer to locally deform in the z direction and prevents proper focus on a stepper, or failure of the stepper to adequately determine optical height when exposing a field. In either case, the effect tends to be perceived by operators as a large-size (~1 mm diameter of more) color change. In the case of full-field defocus, the entire field exhibits a "color change." The color changes are related to the change in diffraction and scattering by the resist, which has been improperly exposed and tends to exhibit rounded "shoulders" and "scumming" at the bottom of resist troughs. Nikon, in particular, provides an automated macroscopic inspector that uses a single 2-dimensional sensor array (e.g., a charge coupled device (CCD)) and orients the wafer on a tilt/spin stage to maximize defocus sensitivity.

Macro inspection devices are being pushed to detect smaller resist pattern defects. This push forces increased spatial resolution in the optical systems. Regretfully, due to the necessary increase in numerical aperture to achieve spatial resolution, directional sensitivity of the diffracted/scattered light is reduced.

Thus, in order to achieve both defocus and small pattern defect detection, it is important to provide separate optical systems for each type of detection. In the past, this has been an expensive proposition due to the addition of electronic sensors and sophisticated optics.

The system illustrated in FIG. 3, however, addresses many of the above disadvantages of currently available macro defect inspection systems. In addition, the system illustrated in FIG. 3 also provides additional advantages described below. For example, the system provides a sensitive defocus channel at minimal cost. The system can also be integrated into other processing equipment particularly the front-end wafer handlers common to most semiconductor processing tools. In one embodiment, the module measurement cell illustrated in FIGS. 1 and 2 may include the inspection system illustrated in FIG. 3 and may be integrated into a processing tool or an inspection system as described above. In addition, the system shown in FIG. 3 provides a high-reliability system by minimizing mechanical moving parts. Furthermore, the system of FIG. 3 accomplishes defocus detection with minimal throughput reduction.

The basic idea behind the system illustrated in FIG. 3 is to leverage the existence of low-resolution electronic sensors to provide simultaneous observation of a wafer from multiple viewing angles by using an array of relatively inexpensive cameras. This approach directly contrasts with Nikon's approach that uses a single sensor and changes the viewing angles by mechanical motion of the wafer and serial image acquisition.

Figure 4:
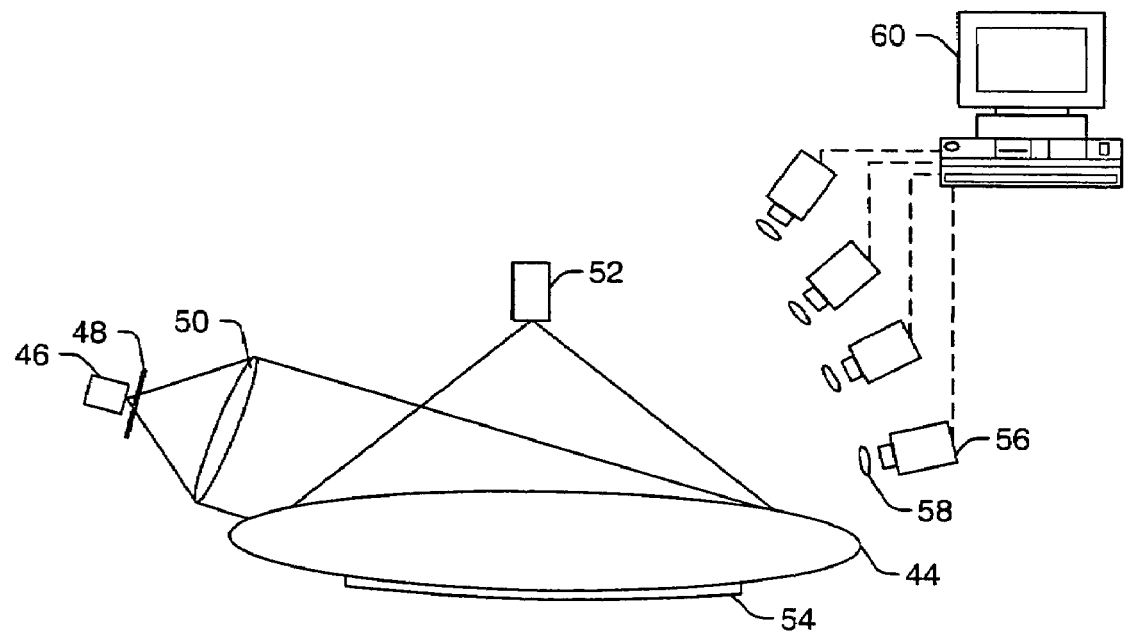

The inspection system includes an illumination subsystem configured to direct light to wafer 44. Although one particular illumination scheme is shown in FIG. 3, it is to be understood that illumination schemes of different varieties can be used in the inspection system. For defocus defect detection, it may be advantageous to use collimated light directed to the wafer. A concept for such a system is depicted in FIG. 3. The illumination subsystem includes light source 46, which in some embodiments is a point light source. The point source could be either a strobe light or an arc lamp. If the point source is an arc lamp, the illumination subsystem may also include one or more optical filters 48 coupled to the point light source, which are shown in the additional embodiment of FIG. 4. The one or more optical filters may be configured to alter a wavelength spectrum of the light directed to the wafer (i.e., to control the spectrum of the light source). As shown in FIGS. 3 and 4, the illumination subsystem may also include collimating lens 50. The collimating lens may be implemented with an inexpensive plastic replicated Fresnel lens. Alternatively, collimation can be achieved by using parabolic mirrors. In some embodiments, collimating lens 50 may be replaced by another lens or a set of lenses. The illumination subsystem may include additional components (not shown) such as polarizing filters or any other suitable optical component known in the art.

In some embodiments, the inspection system may also include additional illumination subsystem 52, as shown in FIG. 4. The illumination subsystem and additional illumination subsystem 52 may be configured to direct light to the wafer at different azimuthal angles. Although the illumination subsystems are shown in FIG. 4 to direct light to a wafer at azimuthal angles that differ by about 90°, it is to be understood that the difference in the azimuthal angles may be less than 90° or greater than 90° and may depend on characteristics of the wafer being inspected. The additional illumination subsystem may be configured as described above. Therefore, additional observations can be made by using multiple light sources at different azimuths with respect to the wafer. Alternatively, a support device such as a spin stage or wafer handler may be configured to rotate the wafer during inspection such that the additional observations may be acquired.

The wafer may be positioned on support device 54, as shown in FIG. 4, which is configured to support the wafer during inspection. In some embodiments, the position of the wafer is substantially static (i.e., there are no moving parts at all). For example, the wafer is not tilted during inspection. In one embodiment, the support device may be a stage suitable for use in an inspection system. Alternatively, the wafer could be positioned on a wafer handler (e.g., on the end-effector of a handler robot). For example, the inspection system may be coupled to a wafer handler of a host inspection system such as that shown in FIG. 2. As an alternative, the inspection system may be coupled to a wafer handler of a process tool (not shown).

As further shown in FIG. 3, the inspection system includes low resolution electronic sensors 56 arranged at multiple viewing angles. The sensors are configured to detect light returned from the wafer substantially simultaneously. Because multiple images of the wafer are acquired in parallel, the time taken for image acquisition is relatively short. Although four electronic sensors are shown in FIG. 3, it is to be understood that the inspection system may include two or more such electronic sensors. As mentioned above, a position of the wafer is substantially constant during inspection. In this manner, the multiple viewing angles of the electronic sensors (although different) may be substantially constant during inspection.

In one embodiment, the electronic sensors may be CCD cameras. In one such embodiment, the output of the electronic sensors may be direct digital readouts. In one particular embodiment, the electronic sensors may be low resolution "web cameras" with typical CCD pixel arrays of 640 pixels×480 pixels and direct digital readout via USB or FireWire buses. In some embodiments, it may be advantageous to use several spectral lines and color imagers in the cameras because the defect classes that are of interest may be detected without high spatial resolution.

In some embodiments, the inspection system may include imaging optics 58 coupled to the electronic sensors, as shown in FIG. 4. Since high spatial resolution is not required for this inspection system, the imaging optics attached to the individual cameras may not be of relatively high quality, and "bad pixels" may be tolerated in the sensor arrays. In addition, optical axes of the imaging optics may not be normal to sensor arrays of the electronic sensors. For example, the imaging optics may include individual lenses coupled to each of the electronic sensors. The lenses may be of the "pan-tilt" variety, where their optical axes are not normal to the sensor arrays. This configuration allows for larger depth-of-focus and elimination of some degree of "Keystone" distortion caused by the perspective of the viewing angles.

The inspection systems shown in FIGS. 3 and 4 also include processor 60. The processor may be coupled to the electronic sensors by a transmission medium, as shown by the dotted lines in FIGS. 3 and 4. Processor 60 is configured to detect defects on the wafer using output generated by the electronic sensors. The defects may be defocus defects, small pattern defects, or a combination thereof. In one embodiment, the processor may also be configured to determine which of the electronic sensors produced images with the largest sensitivity to defocus defects. The processor may use an algorithm to select the images with the largest sensitivity to defocus among the various sensors. In such an embodiment, the processor may be further configured to select the images with the largest sensitivity for use in defect detection. In another embodiment, the processor may be configured to assign common coordinates to the images produced by the sensors and to compare the images produced by different sensors. Therefore, images acquired with different sensors can be compared to one another after proper interpolation to a common coordinate system.

Inspection of the backside of a wafer provides information about contamination of the backside of the wafer. It was identified that contamination of the backside of a wafer can create problems on the frontside of the wafer. For example, a particle on the backside of a wafer may affect the flatness of the wafer locally, and thus may create defocus or hot spots on the frontside of the wafer during lithography. Thus, certain frontside problems may be caused by backside contamination. Examples of methods for correlating backside defects to frontside defects on a wafer are illustrated in U.S. Patent Application Ser. Nos. 60/416,136 entitled "Methods for Correlating Backside and Frontside Defects Detected on a Specimen and Classification of Backside Defects," filed on Oct. 4, 2002 and 10/678,883 entitled ""Methods for Correlating Backside and Frontside Defects Detected on a Specimen and Classification of Backside Defects," filed on Oct. 3, 2003, which are incorporated by reference as if fully set forth herein. In addition, defect source analysis (DSA) may be used to analyze frontside defects with respect to backside defects. This analysis would give the "difference" in the two scans. However, the backside scan of a wafer usually contains other information such as chuck, handler, and/or aligner imprint(s), which may not be of interest to the analysis. As such, it would be advantageous to remove such imprint(s) from the backside scan data or the "difference" in the two scans.

In one embodiment, the method includes selecting a template corresponding to a support device that contacts a backside of a wafer prior to inspection of the backside of the wafer. The support device may be a chuck, a stage, an aligner, or a wafer handler. In some embodiments, selecting the template may include accessing information related to processes performed on the wafer. For example, a fab database may include information related to any of the processes performed in a fab such as tool history, wafer history, and reticle history. A fab database may also include any set of data suitable for use in an overall fab management system. An example of such a system is illustrated in PCT Publication No. WO 99/59200 to Lamey et al., which is incorporated by reference as if fully set forth herein. For example, the computer-implemented method may include accessing a fab database and sending information about the tool history, wafer history, and/or reticle history to a processor configured to perform the methods described herein.

Template data can be created for chucks, stages, aligners, and handlers of interest. In some embodiments, the method may include creating data representing the template using computer-aided design (CAD). In a different embodiment, the method may include creating data representing the template by inspecting a backside of two or more wafers contacted by the support device and extracting common information from inspection data for the two or more wafers. Any other method for creating template data may also be used.

In addition, the method includes subtracting data representing the template from the inspection data generated by the inspection of the backside of the wafer to generate data representing defects on the backside of the wafer. Template subtraction may be event-based or signature-based. The data representing the defects may be subtracted from data generated by inspection of a frontside of a wafer. Alternatively, the inspection data from which the template data is subtracted may be generated by subtracting backside inspection data from data generated by inspection of a frontside of a wafer. In this manner, the template may be subtracted from one of the following: (1) backside scan data prior to subtraction from frontside scan data or (2) difference scan data that represents the difference between backside scan data and frontside scan data.

In some embodiments, the defects detected on the backside of the wafer may be caused by the support device. In this manner, template subtraction may be used to monitor the contamination of the backside of a wafer on or off of a tool due to the support device(s). Given a fixed template for a support device, this template data can be subtracted from backside inspection data. The subtracted information will give a measure of contamination contributed by the support device of interest. This level of contamination can be examined for each wafer and/or progressively for consecutive wafers. In the former case, an alarm may be triggered if the contamination level exceeds a certain limit. In the latter case, the rate of contamination due to the support device of interest may be monitored. Such analysis may be performed and used offline.

The method may also include classifying the defects on the backside of the wafer. In addition, the method may include correlating the defects on the backside of the wafer to defects detected on a frontside of the wafer as described above.

Figure 5:
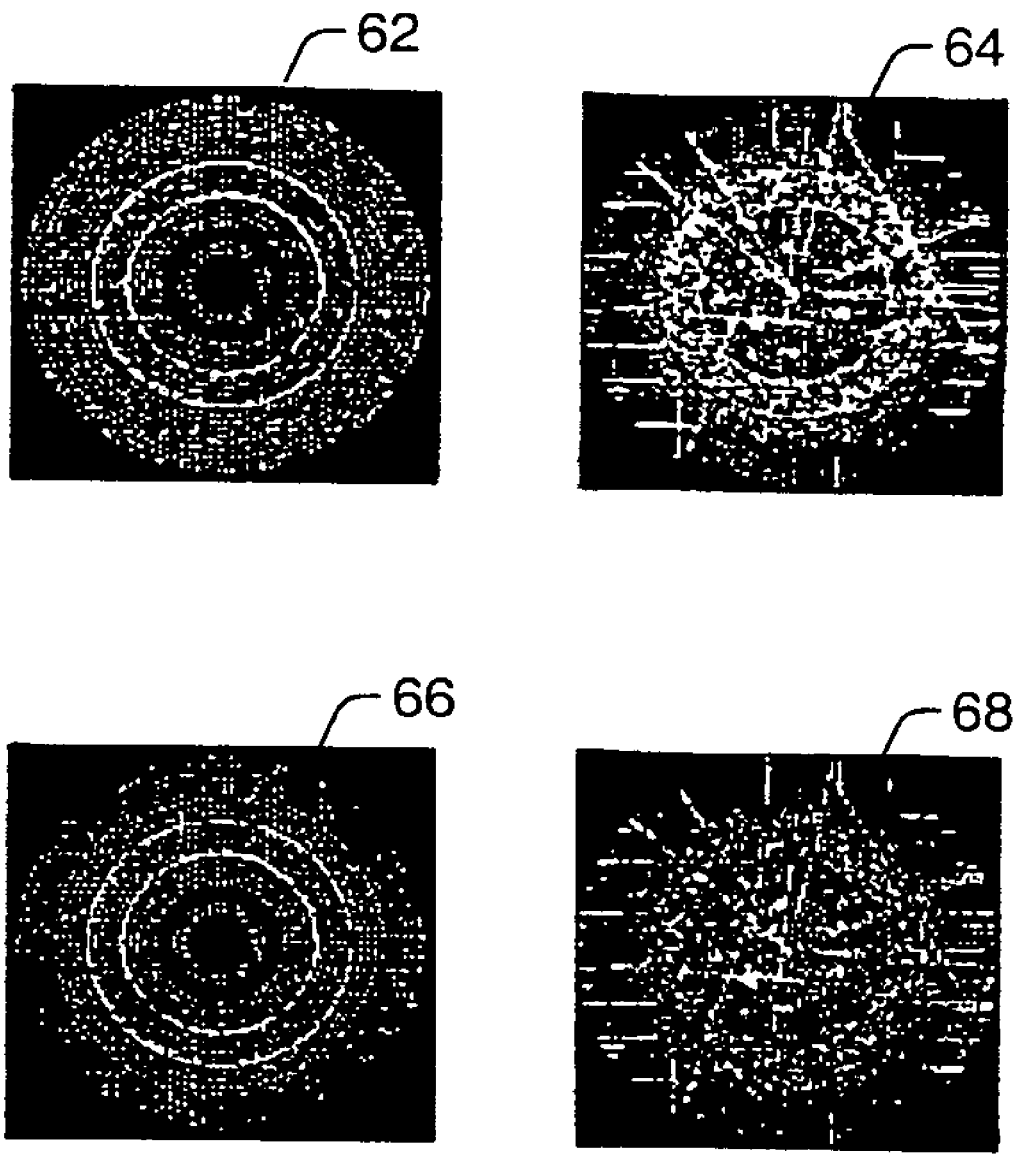
FIG. 5 depicts images of example data that illustrate a method for analyzing inspection data.

FIG. 5 depicts images of example data that illustrate a method for analyzing inspection data, and particularly backside inspection data. Image 62 illustrates template data generated by a raw backside scan. For demonstration purposes, input data 64 was created by adding simulated events to a different backside scan for the same chuck. Image 66 illustrates the common features of image 62 and input data 64. These features correspond to the events correlated with the chuck imprint, and subtraction of these features from the input data reveals information 68, which is useful for further analysis and/or classification of the backside defects using a technique such as clustering, spatial signature analysis (SSA), and DSA with the frontside defects. The methods described above may be performed by one of the processors described above (e.g., processor 42). The processor may be configured to use any algorithms or methods to perform the above described methods.

In an embodiment, the methods described above may include altering one or more parameters of a process tool in response to defects detected on the frontside, edge, and/or backside of a wafer using a feedback control technique or a feedforward control technique. The process tool may be, for example, a lithography tool, an etch tool, a chemical-mechanical polishing (CMP) tool, a deposition tool, a plating tool, or a cleaning tool. The parameter(s) may be altered preferably to reduce defects on the wafer or on additional wafers that are processed in the process tool. In a further embodiment, a processor as described herein may be coupled to the process tool and may be configured to alter one of more parameters of the process tool in response to defects detected on the frontside, edge, or backside of a wafer using a feedback control technique or a feedforward control technique.

Program instructions implementing methods such as those described above may be transmitted over or stored on a carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a processor may be configured to execute the program instructions to perform a computer-implemented method according to the above embodiments. The processor may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

Further modifications and alternative embodiments of various aspects of the invention may be apparent to those skilled in the art in view of this description. For example, wafer inspection systems and methods for analyzing inspection data are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An inspection system, comprising:
    a module measurement cell coupled to a host inspection system by a wafer handler, wherein the host inspection system is configured as a stand alone tool, and wherein the module measurement cell is configured to inspect a wafer using one or more modes prior to inspection of the wafer by the host inspection system; and
    a processor coupled to at least the module measurement cell, wherein the processor is configured to detect defects on the wafer using output produced by the module measurement cell, and wherein the processor is further configured to use the output to determine if the wafer has backside contamination above a predetermined level and to determine that the wafer is not to be inspected by the host inspection system if the backside contamination is above the predetermined level.

2. The system of claim 1, wherein the one or more modes comprise backside inspection, edge inspection, frontside macro defect inspection, or a combination thereof.

3. The system of claim 1, wherein the module measurement cell is further configured to perform frontside macro defect inspection as the wafer is being moved into the module measurement cell by the wafer handler.

4. The system of claim 1, wherein the module measurement cell comprises an optical character recognition subsystem, a barcode reader subsystem, an alignment subsystem, or a combination thereof.

5. The system of claim 1, wherein the host inspection system is further configured to inspect an additional wafer while the module measurement cell is inspecting the wafer.

6. The system of claim 1, wherein the processor is further configured to use the output to determine if the inspection of the wafer by the host inspection system is to be performed.

7. The system of claim 1, wherein the processor is further configured to use the output to determine if the wafer must be reworked and to determine that the wafer is not to be inspected by the host inspection system if the wafer must be reworked.

8. The system of claim 1, wherein the module measurement cell is further configured as an additional host inspection module.

9. The system of claim 1, wherein the module measurement cell comprises an inspection subsystem, wherein the inspection subsystem comprises an illumination subsystem configured to direct light to the wafer and two or more low resolution electronic sensors arranged at multiple viewing angles, wherein the two or more sensors are configured to detect light returned from the wafer substantially simultaneously, and wherein the processor is further configured to detect the defects on the wafer using output generated by the two or more sensors.

10. The system of claim 9, wherein the illumination subsystem comprises a point light source.

11. The system of claim 10, wherein the illumination subsystem further comprises one or more optical filters coupled to the point light source, and wherein the one or more optical filters are configured to alter a wavelength spectrum of the light directed to the wafer.

12. The system of claim 9, wherein the light directed to the wafer comprises collimated light.

13. The system of claim 9, wherein the inspection subsystem further comprises an additional illumination subsystem, and wherein the illumination subsystem and the additional illumination subsystem are configured to direct light to the wafer at different azimuthal angles.

14. The system of claim 9, wherein the multiple viewing angles are substantially constant during inspection by the inspection subsystem.

15. The system of claim 9, wherein a position of the wafer is substantially constant during inspection by the inspection subsystem.

16. The system of claim 9, further comprising a support device configured to spin the wafer during inspection by the inspection subsystem.

17. The system of claim 9, wherein the two or more sensors comprise CCD cameras, and wherein the output generated by the two or more sensors comprises direct digital readouts.

18. The system of claim 9, wherein the processor is further configured to determine which of the two or more sensors produces images with the largest sensitivity to defocus defects, and wherein the processor is further configured to select the images with the largest sensitivity for use in defect detection.

19. The system of claim 9, wherein the output generated by the two or more sensors comprises images, and wherein the processor is further configured to assign common coordinates to the images and to compare the images produced by different sensors.

20. The system of claim 9, wherein the inspection subsystem further comprises imaging optics coupled to the two or more sensors, and wherein optical axes of the imaging optics are not normal to sensor arrays of the two or more sensors.

21. The system of claim 9, wherein the defects detected by the processor using the output generated by the two or more sensors comprise defocus defects, small pattern defects, or a combination thereof.

22. The system of claim 1, wherein the processor is further configured to select a template that corresponds to a support device that contacts a backside of the wafer prior to inspection of the backside of the wafer and to subtract data representing the template from inspection data generated by the inspection of the backside of the wafer to generate data representing defects on the backside of the wafer.

23. The system of claim 22, wherein the support device comprises a chuck, a stage, an aligner, or a wafer handler.

24. The system of claim 22, wherein the processor is further configured to create the data representing the template using computer-aided design.

25. The system of claim 22, wherein the processor is further configured to create the data representing the template by inspecting a backside of two or more wafers contacted by the support device and extracting common information from inspection data generated by inspecting the backside of the two or more wafers.

26. The system of claim 22, wherein the processor is further configured to subtract the data representing the defects on the backside of the wafer from data generated by inspection of a frontside of the wafer.

27. The system of claim 22, wherein the inspection data is further generated by subtracting backside inspection data from data generated by inspection of a frontside of the wafer.

28. The system of claim 22, wherein the processor is further configured to classify the defects on the backside of the wafer.

29. The system of claim 22, wherein the processor is further configured to correlate the defects detected on the backside of the wafer to defects detected on a frontside of the wafer.

30. The system of claim 22, wherein the defects on the backside of the wafer comprise defects caused by the support device.

* * * * *